US011547398B2

(12) United States Patent
Pereira et al.

(10) Patent No.: US 11,547,398 B2
(45) Date of Patent: Jan. 10, 2023

(54) IMPLANT FIXATION DEVICES AND METHODS OF USING THE SAME

(71) Applicant: Boston Scientific Scimed, Inc., Maple Grove, MN (US)

(72) Inventors: Peter J. Pereira, Mendon, MA (US); Joseph Gordon, Mansfield, MA (US); Shane Siwinski, Providence, RI (US); Faith David-Hegerich, Holliston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 301 days.

(21) Appl. No.: 15/354,524

(22) Filed: Nov. 17, 2016

(65) Prior Publication Data
US 2017/0143463 A1    May 25, 2017

Related U.S. Application Data

(60) Provisional application No. 62/257,499, filed on Nov. 19, 2015.

(51) Int. Cl.
| | |
|---|---|
| *A61F 2/00* | (2006.01) |
| *A61B 17/04* | (2006.01) |
| *A61B 17/06* | (2006.01) |
| *A61B 17/00* | (2006.01) |
| *A61B 17/29* | (2006.01) |

(52) U.S. Cl.
CPC ...... *A61B 17/0469* (2013.01); *A61B 17/0487* (2013.01); *A61B 17/06004* (2013.01); *A61F 2/0036* (2013.01); *A61B 2017/00805* (2013.01); *A61B 2017/0608* (2013.01); *A61B 2017/2927* (2013.01)

(58) Field of Classification Search
CPC ............. A61F 2/0036; A61B 17/06066; A61B 17/06166; A61B 17/0469; A61B 17/0491; A61B 17/0482; A61B 17/0483; A61B 17/062; A61B 2017/0498; A61B 17/00; A61B 17/12; A61B 17/0487; A61B 2017/0422; A61B 2017/0425; A61B 2017/0424; A61B 2017/0488; A61B 2017/049; A61B 17/06004; A61B 2017/00805; A61B 2017/0608; A61B 2017/2927; D05B 97/02
USPC ........................................................ 112/169
See application file for complete search history.

(56) References Cited

U.S. PATENT DOCUMENTS

| | | | | |
|---|---|---|---|---|
| 2,884,478 | A | * | 4/1959 | Becker ................... H01R 4/186 |
| | | | | 174/94 R |
| 5,665,096 | A | * | 9/1997 | Yoon .................. A61B 17/0469 |
| | | | | 606/139 |
| 5,665,109 | A | * | 9/1997 | Yoon .................. A61B 17/0469 |
| | | | | 606/139 |
| 5,879,371 | A | | 3/1999 | Gardiner et al. |
| 6,409,743 | B1 | | 6/2002 | Fenton |

(Continued)

*Primary Examiner* — Jing Rui Ou
(74) *Attorney, Agent, or Firm* — Brake Hughes Bellermann LLP

(57) ABSTRACT

According to an aspect, a medical device includes an elongate member, a needle, and a suture. The needle is movably coupled to the elongate member. The suture is disposed within a lumen defined by the elongate member. The suture has a coupling member coupled to a first portion of the suture. The coupling member is configured to be coupled to a second portion of the suture.

15 Claims, 5 Drawing Sheets

(56) References Cited

U.S. PATENT DOCUMENTS

| | | | |
|---|---|---|---|
| 6,475,229 B1 | 11/2002 | Pagedas | |
| 2002/0193809 A1* | 12/2002 | Meade | A61B 17/0491 606/144 |
| 2003/0093091 A1* | 5/2003 | Paolitto | A61B 17/0487 606/139 |
| 2006/0041263 A1* | 2/2006 | Chu | A61B 17/0491 606/144 |
| 2006/0282088 A1* | 12/2006 | Ryan | A61B 17/0469 606/144 |
| 2008/0300629 A1* | 12/2008 | Surti | A61B 17/0401 606/232 |
| 2009/0024145 A1* | 1/2009 | Meade | A61B 17/06114 606/144 |
| 2009/0069847 A1* | 3/2009 | Hashiba | A61B 17/0487 606/232 |
| 2009/0076546 A1* | 3/2009 | Ashley | A61B 17/0487 606/232 |
| 2009/0138029 A1* | 5/2009 | Saliman | A61B 17/0469 606/144 |
| 2009/0143821 A1* | 6/2009 | Stupak | A61B 17/0057 606/232 |
| 2009/0177031 A1* | 7/2009 | Surti | A61B 1/00087 600/106 |
| 2010/0056861 A1* | 3/2010 | Spivey | A61B 1/018 600/106 |
| 2010/0152751 A1* | 6/2010 | Meade | A61B 17/0469 606/144 |
| 2010/0204731 A1* | 8/2010 | Hart | A61B 17/0401 606/232 |
| 2011/0270279 A1* | 11/2011 | Badhwar | A61B 17/062 606/144 |
| 2012/0089193 A1* | 4/2012 | Stone | A61B 17/0401 606/301 |
| 2012/0165865 A1* | 6/2012 | Fujisaki | A61B 17/0487 606/232 |
| 2012/0277768 A1* | 11/2012 | Viola | A61B 17/0469 606/145 |
| 2013/0041388 A1* | 2/2013 | Lane | A61B 17/0467 606/145 |
| 2014/0214038 A1* | 7/2014 | Sholev | A61B 17/0483 606/79 |

* cited by examiner

IMPLANT FIXATION DEVICES AND METHODS OF USING THE SAME

CROSS-REFERENCE TO RELATED APPLICATION

This application is a Nonprovisional of, and claims priority to, U.S. Patent Application No. 62/257,499, filed on Nov. 19, 2015, entitled "IMPLANT FIXATION DEVICES AND METHODS OF USING THE SAME", which is incorporated by reference herein in its entirety.

TECHNICAL FIELD

This disclosure relates generally to medical devices and more particularly to medical devices that are configured to place or couple bodily implants within a body of a patient.

BACKGROUND

A variety of medical procedures are performed to provide support to portions of a body of a patient. For example, some medical procedures are performed to treat various female pelvic dysfunctions, including procedures to treat urinary incontinence, and correcting various prolapse conditions such as uterine prolapse, cystoceles, rectoceles, and vaginal vault prolapse.

Some such medical procedures have included placing implants within the pelvic region of the patient. Some of the implants are delivered to the pelvic region of the patient through one or more vaginal incisions, and/or through exterior incisions in the patient.

Often such implants are delivered or placed within the body of the patient and coupled or attached to various locations within the body using a series of sutures or knots. For example, in procedures such as sacrocolpopexy procedures, a suture may be tied 4 to 8 times to form a single knot and a series of 12 of more knots may be used to secure an implant within the body of the patient. Accordingly, a procedure for placing and attaching an implant within a body of a patient may require time and skill.

Accordingly, it may be desirable to provide a delivery or coupling tool that includes components or features that would facilitate the delivery and/or attachment process of implants within a body of a patient.

SUMMARY

According to an aspect, a medical device includes an elongate member, a needle, and a suture. The needle is movably coupled to the elongate member. The suture is disposed within a lumen defined by the elongate member. The suture has a coupling member coupled to a first portion of the suture. The coupling member is configured to be coupled to a second portion of the suture.

In some embodiments, the needle includes a curved portion. In some embodiments, the needle includes a curved portion and is configured to rotate with respect to the elongate member.

In some embodiments, the coupling member has a first portion and a second portion, the first portion of the coupling member is coupled to the first portion of the suture, the second portion of the coupling member is configured to be coupled to the second portion of the suture. In some embodiments, the elongate member includes a proximal portion and a distal portion, the distal portion being configured to move with respect to the proximal portion. In some embodiments, the elongate member includes a proximal portion and a distal portion, the distal portion being rotatably coupled to the proximal portion.

In some embodiments, a pusher configured to force at least a portion of the coupler through a wedge feature of the elongate member. In some embodiments, the device includes an actuation member, the actuation member being movably coupled to the elongate member. In some embodiments, the device includes an actuation member, the actuation member being slideably coupled to the elongate member.

In some embodiments, the elongate member includes proximal portion and a distal portion, the distal portion being movably coupled to the proximal portion, the medical device further includes an actuation member, the actuation member being movably coupled to the distal portion of the elongate member.

In some embodiments, the elongate member is configured to be at least partially inserted into a body of a patient. In some embodiments, the elongate member is configured to be at least partially inserted into a body of a patient through a 5 mm to a 12 mm port.

In some embodiments, the needle includes an end portion that is configured to pierce bodily tissue. In some embodiments, the needle includes a sharp end portion that is configured to pierce bodily tissue. In some embodiments, the needle is configured to be removably coupled to the suture.

In another aspect, a medical device includes an elongate member, a needle, and an actuation member. The elongate member defines a lumen. The lumen is configured to receive a suture. The needle is movably coupled to the elongate member. The actuation member is movably coupled to the elongate member. The needle is configured to move with respect to the elongate member in response to the actuation member being moved with respect to the elongate member.

In some embodiments, the elongate member includes proximal portion and a distal portion, the distal portion being movably coupled to the proximal portion, the actuation member being movably coupled to the distal portion of the elongate member.

In some embodiments, the needle includes a curved portion. In some embodiments, the needle includes a curved portion and is configured to rotate with respect to the elongate member.

In some embodiments, the elongate member includes a proximal portion and a distal portion, the distal portion being configured to move with respect to the proximal portion. In some embodiments, the elongate member includes a proximal portion and a distal portion, the distal portion being rotatably coupled to the proximal portion.

In some embodiments, the device includes a pusher configured to force at least a portion of the coupler through a wedge feature of the elongate member.

In another aspect, a method includes inserting at least a portion of a medical device into a body of a patient, the medical device including an elongate member, the elongate member defining a lumen, the lumen configured to receive a suture; a needle movably coupled to the elongate member; and an actuation member; and pressing the actuation member against a portion of the body of the patient such that the actuation member moves with respect to the elongate member.

In some embodiments, the inserting includes inserting at least a portion of the medical device into the body of the patient such that a bodily implant is disposed between the actuation member and the portion of the body of the patient.

In some embodiments, the method includes coupling the needle to a suture.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

The term patient may hereafter be used for a person who benefits from the medical device or the methods disclosed in the present application. For example, the patient can be a person whose body is operated through the medical device or the method disclosed by the present invention. For example, in some aspects, the patient may be a human female, a human male, or any other mammal.

The terms proximal and distal described in relation to various devices, apparatuses, and components as discussed in the subsequent text of the present application are referred with a point of reference. The point of reference, as used in this description, is a perspective of an operator. The operator may be a surgeon, a physician, a nurse, a doctor, a technician, and the like who may perform the procedure and operate the medical device as described in the present invention. The term proximal refers to an area or portion that is closer or closest to the operator during a surgical procedure. The term distal refers to an area or portion that is farther or farthest from the operator.

Figure 1:
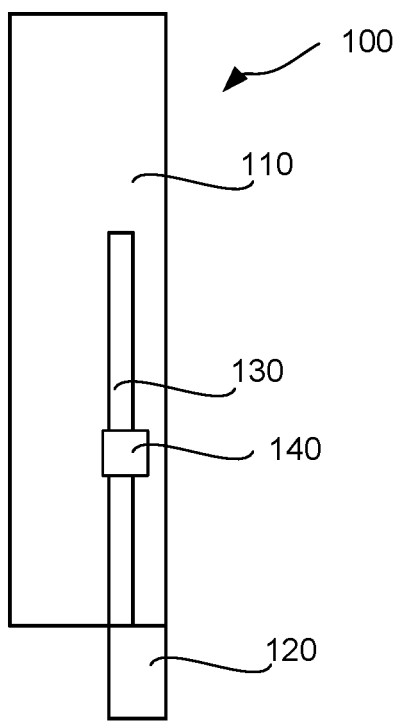
FIG. 1 is a schematic illustration of a medical device according to an embodiment.

FIG. 1 is a schematic illustration of a medical device 100 according to an embodiment of the invention. The medical device 100 may be used to couple or attach a bodily implant within a body of a patient. For example, the medical device 100 may be used to couple or attach an implant within a pelvic region of a patient. For example, in some embodiments, the medical device 100 may be used in a sacrocolpopexy procedure to couple an implant to a vagina or tissue proximate a vagina of a patient. In other embodiments, the medical device 100 may be used to couple or attach different types of bodily implants into different locations within the body of the patient. In other embodiments, the medical device 100 may be used to couple one portion of bodily tissue to another portion of bodily tissue.

The medical device 100 includes an elongate member 110, a needle 120, and a suture 130. The elongate member 110 is configured to be at least partially disposed within a body of a patient. For example, in some embodiments, the elongate member 110 is sized such that it may be inserted into the body of the patient laparoscopically. In some embodiments, the medical device 100 including the elongate member 110 is sized and configured to be inserted into the body of the patient via a port or trocar. In some embodiments, the port or trocar is between 5 mm and 12 mm in size.

The needle 120 is movably coupled to the elongate member 110. In some embodiments, the device 100 includes an actuator that when actuated causes the needle 120 to move with respect to the elongate member 110. In some embodiments, the needle 120 includes a sharp portion or end that is configured to pierce bodily tissue or otherwise lead the remainder of the needle 120 through bodily tissue.

In some embodiments, the needle 120 is configured to move with respect to the elongate member 110 in a circular or substantially circular path. For example, in some embodiments, the elongate member 110 defines a track. The track may be circular, substantially circular, or semi-circular. In such embodiments, the needle 120 may be configured to move within the track defined by the elongate member 110. In some embodiments, the needle 120 is non-linear or includes a curved portion.

The suture 130 is configured to be placed within the body of the patient. In some embodiments, the suture 130 is configured to help retain an implant in place within the body of the patient. For example, in some embodiments, the suture 130 is configured to be passed through a bodily implant and through bodily tissue and form a loop or ring to thereby couple the bodily implant to the bodily tissue. Similarly, in some embodiments, the suture 130 is configured to help secure one portion of bodily tissue to another portion of bodily tissue. The suture 130 may be formed of any type of biocompatible material.

In some embodiments, a coupler 140 is coupled to the suture 130. The coupler 140 is configured to be coupled to the suture 130 to facilitate the formation of a loop or a ring by the suture 130. In some embodiments, the coupler 140 includes a first portion and a second portion. In some embodiments, the first portion of the coupler is coupled to a first portion of the suture 130 and the second portion of the coupler is configured to be coupled to a second portion of the suture.

In use, the medical device 100 may be inserted into the body of a patient. For example, the medical device 100 may be inserted into a pelvic region or another portion of the patient. In some embodiments, the medical device 100 is sized and shaped to fit within and be introduced into the body of the patient via a 5 mm-12 mm trocar. The medical device 100 may be positioned within the body such that a distal end portion of the elongate member 110 is disposed adjacent or abutting a bodily implant and/or bodily tissue.

The needle 120 may then be moved with respect to the elongate member 110. In some embodiments, actuation or movement of an actuator causes the needle 120 to move with respect to the elongate member 110. In some embodiments, the needle 120 is coupled to the suture 130 and the movement of the needle 120 includes moving the needle 120 through a bodily implant and bodily tissue such that the suture extends though the bodily implant and the bodily tissue. In some embodiments the movement of the needle 120 causes a portion of the suture 130 to engage the coupler 140 such that the portion of the suture 130 may be coupled to the coupler 140. Thus, the suture 130 forms a complete loop or ring to help couple the bodily implant to the bodily tissue.

In some embodiments, the medical device 100 may then be moved to another location within the body of the patient and the process may be repeated to form another suture loop or ring that helps couple another portion of the bodily implant to bodily tissue. In some embodiments, the medical device 100 may be used (without being removed from the body of the patient) to place 2, 3, 5, or more suture loops or rings within the body of the patient.

Figure 2:
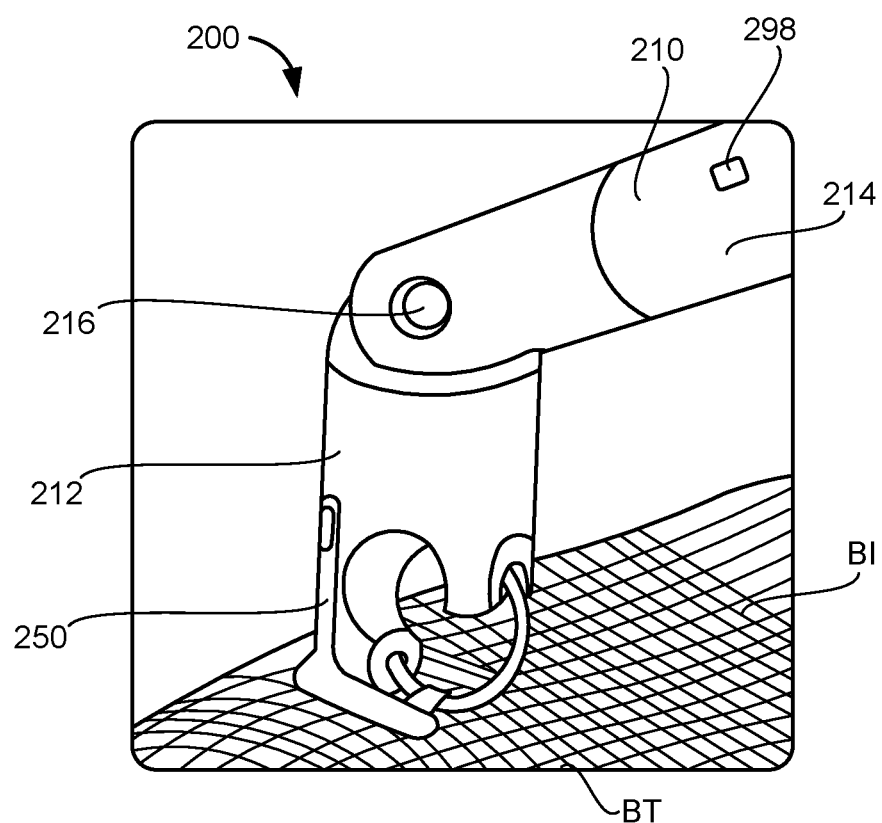
FIG. 2 is a perspective view of a medical device according to an embodiment schematically disposed within a body of a patient.

FIG. 2 is a perspective view of a medical device 200 according to an embodiment of the invention. The medical device 200 may be used to couple or attach a bodily implant within a body of a patient. For example, the medical device 200 may be used to couple or attach an implant within a pelvic region of a patient. For example, in some embodiments, the medical device 200 may be used in a sacrocolpopexy procedure to couple an implant to a vagina or tissue proximate a vagina of a patient. In other embodiments, the medical device 200 may be used to couple or attach different types of bodily implants into different locations within the body of the patient. In other embodiments, the medical device 200 may be used to couple one portion of bodily tissue to another portion of bodily tissue.

Figure 3:
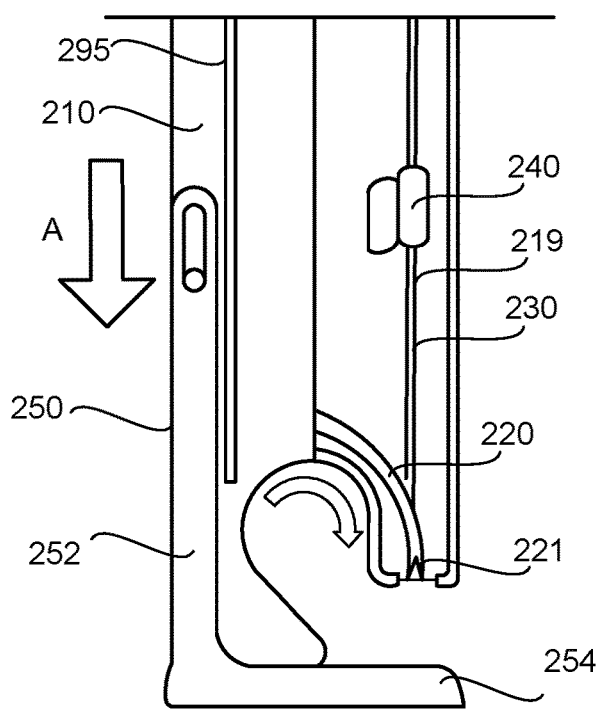
FIGS. 3 and 4 are side views of the medical device of FIG. 2.
Figure 4:
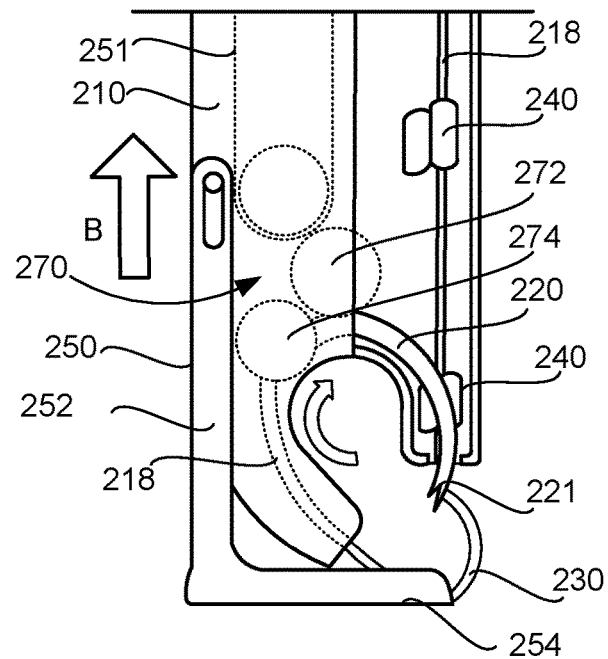

The medical device 200 includes an elongate member 210, a needle 220, and a suture 230. FIGS. 3 and 4 are see-through side views of a distal end portion of the elongate member 210.

The elongate member 210 is configured to be at least partially disposed within a body of a patient. For example, in some embodiments, the elongate member 210 is sized such that it may be inserted into the body of the patient laparoscopically. In some embodiments, the medical device 200 including the elongate member 210 is sized and configured to be inserted into the body of the patient via a port or trocar. In some embodiments, the port or trocar is between 5 mm and 12 mm in size.

In the illustrated embodiment, the elongate member 210 includes a first or distal portion 212 and a second or proximal portion 214. The first portion 212 is configured to move with respect to the second portion 214. Specifically, in the illustrated embodiment, the first portion 212 is pivotally coupled to the second portion 214. A pin 216 extends through at least a portion of the first portion 212 and through at least a portion of the second portion 214 to pivotally couple the first portion 212 of the elongate member 210 to the second portion 214 of the elongate member 210.

The needle 220 is movably coupled to the elongate member 210. In the illustrated embodiment, the needle 220 includes first end portion 221. The first end portion 221 includes a sharp portion or end that is configured to pierce bodily tissue or otherwise lead the remainder of the needle 220 through bodily tissue. The needle 220 also includes a second end portion 223. As best illustrated in FIGS. 5-8 and as discussed in more detail below, the second end portion 223 of the needle 220 includes a coupling portion that is configured to be removably coupled to the suture 230. In the illustrated embodiment, the needle 220 is non-linear or includes a curved portion.

The needle 220 is configured to move with respect to the elongate member 210 in a circular or substantially circular path. In the illustrated embodiment, the elongate member 210 defines a track 218. The track 218 may be circular, substantially circular, or semi-circular. The needle 220 is configured to move within the track or channel 218 defined by the elongate member 210.

In the illustrated embodiment, the medical device 200 includes an actuator 250. The actuator 250 is movably coupled to the elongate member 210. The actuator 250 is configured to control the path of the needle 220 with respect to the bodily tissue. For example, in the illustrated embodiment, the actuator 250 may help control the depth at which the needle 220 penetrates or is inserted into the bodily tissue. For example, in the illustrated embodiment, the actuator 250, when in its actuated state (as illustrated in FIG. 3), extends a distance from the distal end of the elongate member 210. The extension from the distal end allows for some control of or limits the depth that the needle 220 pierces the bodily tissue. In some embodiments, the actuator 250 extends a few millimeters from the distal end of the elongate member 210. For example, in some embodiments, the actuator 250 may extend such that the needle 220 may penetrate the bodily tissue (such as the vaginal wall) at a depth of 1 to 2 mm. In other embodiments, the actuator 250 may extend such that the needle 220 may penetrate the bodily tissue at a depth greater than 2 mm.

Figure 10:
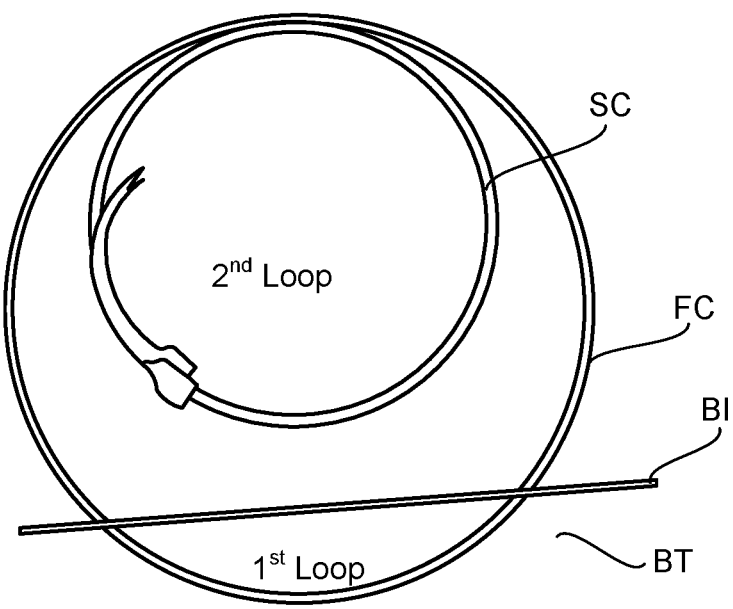
FIG. 10 is a schematic illustration of the movement of a needle of the medical device of FIG. 2.

Additionally, when the actuator 250 is in its unactuated state (as illustrated in FIG. 4), the needle 220 may be moved along its second pass or make or form its second loop (as illustrated in FIG. 10). In some embodiments, the second pass or second loop of the needle 220 does not include a passing of the needle 220 through bodily tissue.

In the illustrated embodiment, the actuator 250 includes an arm portion 252 and a base portion 254. The actuator 250 is configured to move or slide longitudinally with respect to the elongate member 210 as illustrated in FIGS. 3 and 4. Specifically, the base portion 254 may be placed against bodily tissue BT (and a bodily implant BI) as illustrated in FIG. 2. The elongate member 210 may then be pressed to move or compress the actuator 250 with respect to the elongate member 210 as illustrated in FIGS. 2 and 3. In the illustrated embodiment, the actuator 250 is biased to its uncompressed or unactuated state (as illustrated in FIG. 4) and can be moved to its actuated state (as illustrated in FIG. 3).

In the illustrated embodiment, an actuation member 298 is operatively coupled to the needle 220 via a series of linkages, such as wheels 270 (shown in dashed lines in FIG. 4) and a pulley system 251. The linkages, such as the wheels 270 and pulley 251, are disposed within the body portion or a lumen defined by the elongate member 210. The actuation member 298 may be any type of actuation member, such as a plunger, a trigger, a button, or another type of member. In the illustrated embodiment, movement of the actuation member 298 causes wheels 272 and 274 to rotate, such as via the pulley 251. The rotation of wheels 272 and 274 cause the needle 220 to move with respect to the elongate member 210. Specifically, rotation of the wheels 272 and 274 cause the needle 220 to move in a circular path and within the channel 218 defined by the elongate member 210. In the illustrated embodiment, the needle 220 is sized such and the wheels 272 and 274 are positioned such that at least one of the wheels 272 and 274 is always in contact with the needle 220. In some embodiments, the wheels 272 and 274 are frictionally coupled to the needle 220. In some embodiments, at least one of the wheels 272 and 274 is in contact with the needle 220 at all times throughout the path of the movement of the needle 220.

The suture 230 is configured to be placed within the body of the patient. In some embodiments, the suture 230 is configured to help retain an implant in place within the body of the patient. For example, in some embodiments, the suture 230 is configured to be passed through a bodily implant and through bodily tissue and form a loop or ring to thereby couple the bodily implant to the bodily tissue. Similarly, in some embodiments, the suture 230 is configured to help secure one portion of bodily tissue to another portion of bodily tissue. The suture 230 may be formed of any type of biocompatible material.

In the illustrated embodiment, the suture 230 is disposed within a lumen 219 defined by the elongate member 210. The suture 230 is configured to move and slide within the lumen 219.

The illustrated embodiment includes coupler 240. Specifically, the device 200 includes a plurality of couplers 240. The coupler 240 is coupled to the suture 230. The coupler 240 is configured to be coupled to the suture 230 to facilitate the formation of a loop or a ring by the suture 230.

Figure 8:
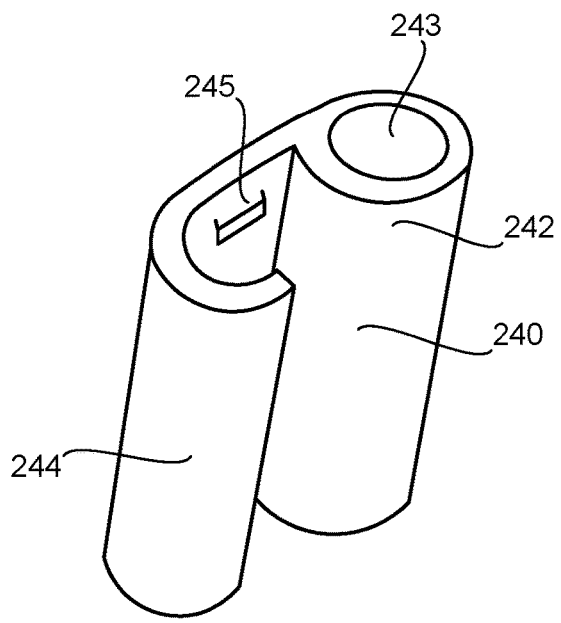
FIG. 8 is a perspective view of a coupler of the medical device of FIG. 2.

As best illustrated in FIG. 8, the coupler 240 includes a first portion 242 and a second portion 244. In some embodiments, the first portion 242 of the coupler 240 is coupled to a first portion of the suture 230 and the second portion 244 of the coupler 240 is configured to be coupled to a second portion of the suture 230. Specifically, in the illustrated embodiment, the first portion 242 of the coupler 240 defines a lumen 243. The suture 230 extends through the lumen 243. In some embodiments, the first portion of the suture 230 is frictionally coupled within the lumen 243 of the first portion 242 of the coupler 240. In some embodiments, a coupler 240 may be crimped or compressed such that the first portion of the suture 230 is coupled to the first portion 242 of the coupler 240. In other embodiments, an adhesive or other coupling material may be used to couple the first portion of the suture 230 to the first portion 242 of the coupler 240. The second portion 244 of the coupler 240 defines a slot 245. The slot 245 is configured to receive and be coupled to a second portion of the suture 230. As will be discussed in more detail below, the second portion 244 of the coupler 240 is configured to be flexed or bent to surround the second portion of the suture 230 to couple the second portion 244 of the coupler 240 to the suture 230.

In use, the medical device 200 may be inserted into the body of a patient. For example, the medical device 200 may be inserted into a pelvic region or another portion of the patient. In some embodiments, the medical device 200 is sized and shaped to fit within and be introduced into the body of the patient via a 5 mm-12 mm trocar. The medical device 200 may be positioned within the body such that a distal end portion of the elongate member 210 or the actuator 250 is disposed adjacent or abutting a bodily implant BI and/or bodily tissue BT (see for example, FIG. 2).

Figures 5, 6, 7:
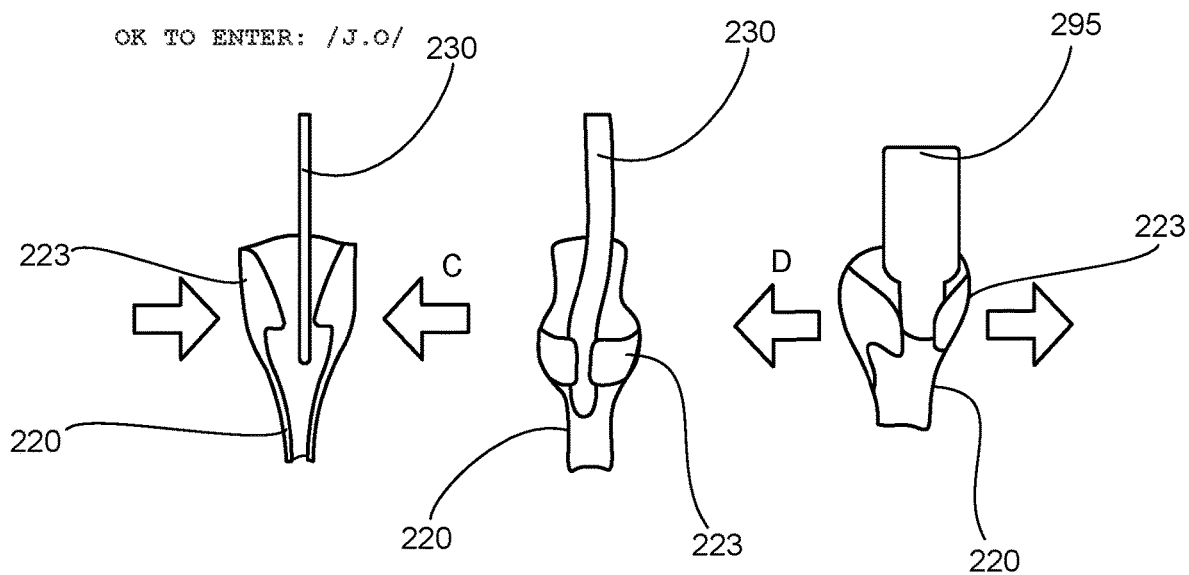
FIGS. 5, 6, and 7 are side views of a portion of a suture according to an embodiment of the invention.

The actuator 250 may then be compressed such that the elongate member 210 moves in the direction of arrow A of FIG. 3 with respect to the actuator 250. Movement of the actuator 250 with respect to the elongate member 210 may help to control or limit the depth of needle penetration of the needle 220 into the bodily tissue. The actuation member 298 may then be actuated to cause the pulley system 251 and the wheels (including wheels 272 and 274) to rotate and move the needle 220 with respect to the elongate member 210. As the needle 220 moves past the lumen 219 and the suture 230, the second end portion 223 of the needle 220 is coupled to the suture 230. Specifically, as illustrated in FIGS. 5 and 6, the suture 230 is received in the coupling portion of the second end portion 223 of the needle and the coupling portion is bent or moved to frictionally couple the suture 230 to the needle 220. In some embodiments, the coupling portion of the needle 220 passes through a crimper or a wedge portion of the elongate member 210 to crimp or move the wings or portions of the coupling portion 223 in the direction of arrow C in FIG. 5.

With the suture 230 coupled to the needle 220, the needle 220 continues on its circular path leading the needle out of the end portion of the elongate member 210 and through any bodily implant and bodily tissue as illustrated in FIG. 2. As best illustrated in FIG. 10, the needle 220 makes two complete circles. The first circle FC passes the suture through the bodily tissue BT and the bodily implant BI. The second circle SC (while the actuator is in its second position as illustrated in FIG. 4) brings the suture 230 back to the location that where the suture was first coupled to the needle 220 (see FIG. 4). As the suture 230 has made the two circles, the suture 230 has been pulled or slid down the lumen 219 defined by the elongate member 210. When the needle makes this second pass, the needle 220 guides the suture 230 though the slot 245 of the second portion 244 of the coupler 240.

Figure 9:
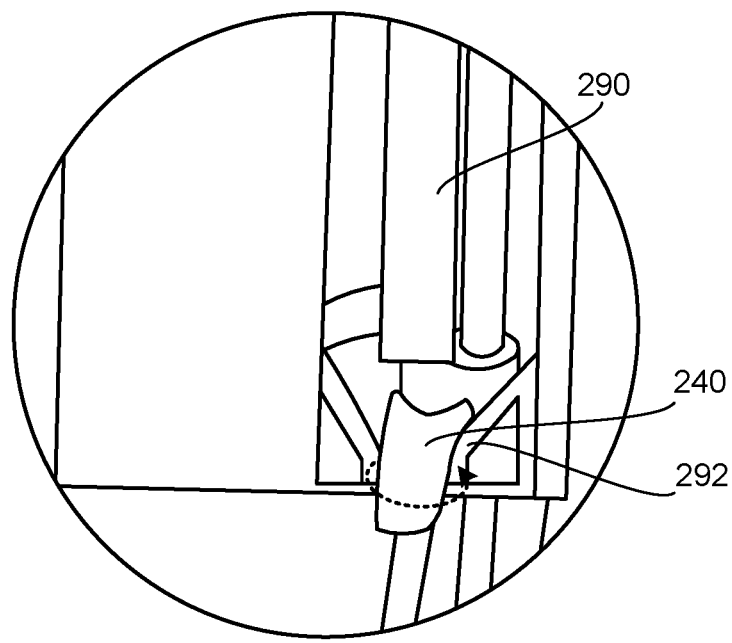
FIG. 9 is a perspective view of a portion of the medical device of FIG. 2.

As best illustrated in FIG. 9, a pusher 290 is configured to push or force the coupler 240 through a wedge shaped feature 292 defined by the elongate member 210. The passing of the coupler 240 through the wedge causes the slot to crimp or close on the suture to frictionally couple that portion of the suture to the coupler 240. In some embodiments, the pusher 290 may be moved or actuated by applying a force to the pusher, for example a force may be applied to the pusher 290 at a proximal end portion or handle portion of the device. In some embodiments, a force may be applied to the pusher 290 by actuating an actuation mechanism.

As best illustrated in FIG. 7, the medical device 200 includes a rod 295. The rod 295 is configured to extend or be forced into the coupling portion 223 of the needle 220 to release the suture 230 from the needle 220. The rod 295 may be actuated by applying a force to the rod. For example, a force may be applied to the rod 295 at a proximal end portion or handle of the device to move the rod 295. In some embodiments, a force may be applied to the rod 295 by actuating an actuation mechanism.

In some embodiments, the suture 230 may then be cut to separate the portion of the suture that has been passed though the bodily tissue from the remainder of the suture that is disposed in the lumen 219 of the elongate member 210. In some embodiments, the medical device includes a cutting tool such as a knife or other object that is configured to cut the suture. In the illustrated embodiment, the coupler 240 includes a ledge or sharp portion that is configured to contact and cut the suture 230.

In some embodiments, the movement of the needle 220 is completed by compressing moving and relaxing the actuation mechanism 298 a single time. In other embodiments, the movement of the needle 220 through its two circles requires more than one compression and relaxation of the actuation member 298. In some embodiments, once the needle 220 is moved to place one suture loop or ring within the body of the patient, the process may be repeated to place additional suture loops or rings within the body of the patient. In some embodiments, several suture loops may be placed without removing the device from the body of the patient to help retain an implant within the body of the patient.

Figure 11:
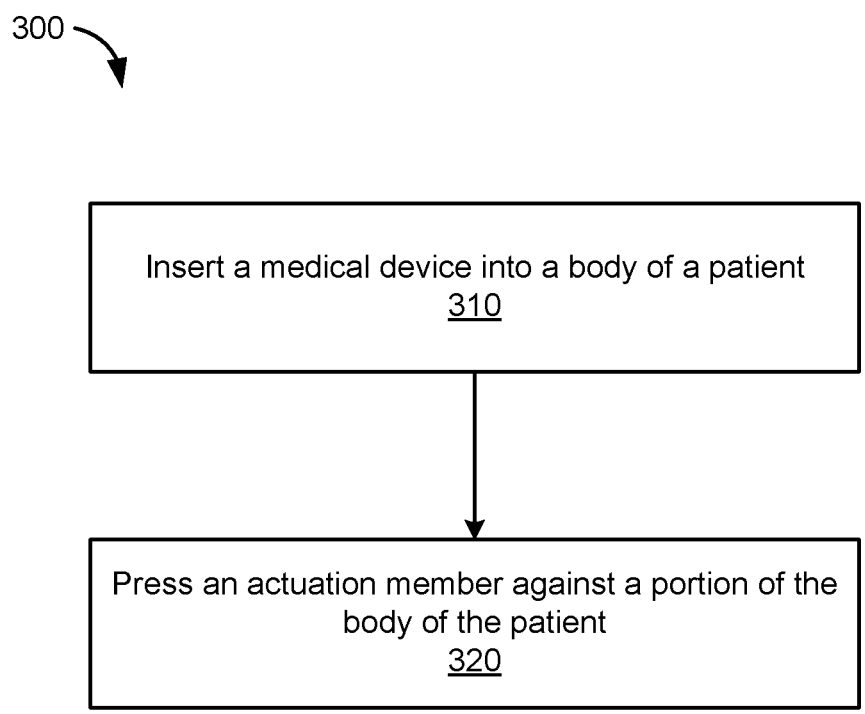
FIG. 11 is a flow chart of a method according to an embodiment.

FIG. 11 is a flow chart for a method 300. The method includes, at 310, inserting a medical device into a body of a patient and at 320, pressing an actuation member of the medical device against a portion of the body of the patient.

In some embodiments, the inserting includes inserting the actuation member into the body of the patient.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device, comprising:
    an elongate member having a first portion, a second portion, and a pin extending through a portion of the first portion and a portion of the second portion to pivotally couple the first portion to the second portion;
    a non-linear needle movably coupled to the elongate member;
    a suture disposed within a lumen defined by the elongate member, the suture having a coupling member coupled to a portion of the suture, the coupling member includes a first portion defining a lumen and a second portion defining a slot, the suture being configured to be frictionally coupled within the lumen of the first portion of the coupling member, the second portion of the coupling member is configured to be compressed such that the suture is coupled to the second portion of the coupling member; and
    an actuation member movably coupled to the elongate member and being configured to cause the needle to move along a substantially circular path with respect to the elongate member.

2. The medical device of claim 1, wherein the needle includes a curved portion.

3. The medical device of claim 1, further comprising:
    a pusher configured to force at least a portion of the coupling member through a wedge feature of the elongate member.

4. The medical device of claim 1, further comprising an actuator, the actuator being slideably coupled to the elongate member.

5. The medical device of claim 1, wherien the first portion and the second portion of the coupling member are adjacent to each other.

6. The medical device of claim 1, wherein the first portion of the coupling member is compressed such that the suture is coupled to the first portion of the coupling member.

7. The medical device of claim 1, further comprising an actuator, the actuator being movably coupled to a distal end portion of the elongate member.

8. The medical device of claim 1, further comprising an actuator configured to control the depth at which the needle penetrates bodily tissue.

9. A method comprising:
    inserting at least a portion of a medical device into a body of a patient, the medical device including:
        an elongate member, the elongate member defining a lumen, the lumen configured to receive a suture, a needle movably coupled to the elongate member,
        a coupling member coupled to a portion of the suture, the coupling member includes a first portion defining a lumen and a second portion defining a slot, the suture being configured to be frictionally coupled within the lumen of the first portion of the coupling member;
        an actuation member, and
        an actuator movably coupled to the elongate member; and
    moving the needle along a substantially circular path,
    wherein the inserting includes inserting at least a portion of the medical device into the body of the patient such that a bodily implant is disposed between the portion of the medical device and a portion of the body of the patient.

10. The method of claim 9, further comprising:
    coupling the needle to a suture.

11. The method of claim 9, wherein the needle includes a curved portion.

12. The method of claim 9, wherein the moving includes moving the needle along a substantially circular path with respect to the elongate member.

13. A medical device, comprising:
    an elongate member having a first portion, a second portion, and a pin extending through a portion of the first portion and a portion of the second portion to pivotally couple the first portion to the second portion;
    a non-linear needle movably coupled to the elongate member;
    a suture disposed within a lumen defined by the elongate member, the suture having a coupling member coupled to a portion of the suture, the coupling member includes a first portion defining a lumen and a second portion defining a slot, the suture being configured to be frictionally coupled within the lumen of the first portion of the coupling member;
    an actuator configured to control the depth at which the needle penetrates bodily tissue; and
    an actuation member movably coupled to the elongate member and being configured to cause the needle to move along a substantially circular path with respect to the elongate member.

14. The medical device of claim 13, wherein the needle includes a curved portion.

15. The medical device of claim 13, further comprising:
    a pusher configured to force at least a portion of the coupling member through a wedge feature of the elongate member.

* * * * *